United States Patent [19]

Barth et al.

[11] 4,432,987
[45] Feb. 21, 1984

[54] CRYSTALLINE BENZENESULFONATE SALTS OF SULTAMICILLIN

[75] Inventors: Wayne E. Barth, East Lyme; Vytautas J. Jasys, New London, both of Conn.

[73] Assignee: Pfizer Inc., New York, N.Y.

[21] Appl. No.: 371,156

[22] Filed: Apr. 23, 1982

[51] Int. Cl.$^3$ .................. A61K 31/43; C07D 499/32
[52] U.S. Cl. ................................ 424/271; 260/239.1
[58] Field of Search ..................... 260/239.1; 424/271

[56] References Cited

U.S. PATENT DOCUMENTS 4,234,579 11/1980 Barth .................................. 424/246
4,244,951 1/1981 Bigham ............................... 424/250

FOREIGN PATENT DOCUMENTS 890649 10/1981 Belgium .
2044255 10/1980 United Kingdom .
2084572 4/1982 United Kingdom .

Primary Examiner—Natalie Trousof
Assistant Examiner—Vera C. Clarke

Attorney, Agent, or Firm—Charles J. Knuth; Albert E. Frost; Paul D. Thomas

[57] ABSTRACT

Novel benzenesulfonic acid addition salts of sultamicillin of the formula

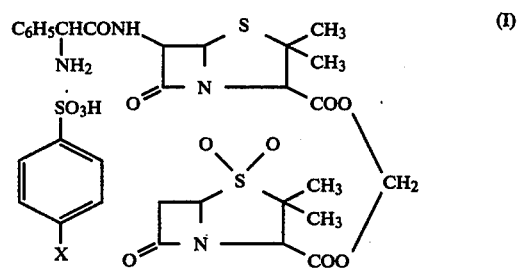

and hydrated forms thereof, where X is hydrogen or chloro, especially the crystalline dihydrate salts, having advantages over the prior art forms of sultamicillin in pharmaceutical dosage forms, most particularly those for use in pediatric medicine, method for their use and pharmaceutical compositions thereof.

8 Claims, No Drawings

CRYSTALLINE BENZENESULFONATE SALTS OF SULTAMICILLIN

BACKGROUND OF THE INVENTION

1. Field of the Invention

The invention relates to certain novel benzenesulfonic acid addition salts of 1,1-dioxopenicillanoyloxymethyl 6-[D-(2-amino-2-phenylacetamido)]penicillanate (sultamicillin) having advantages for use in antibacterial formulations.

2. Description of the Prior Art

Barth, in U.S. Pat. No. 4,234,579 issued Nov. 18, 1980, discloses penicillanic acid 1,1-dioxide (sulbactam) and esters thereof which are readily hydrolyzable in vivo, useful as antibacterial agents and for enhancing the effectiveness of beta-lactam antibiotics, such as ampicillin, against many beta-lactamase producing bacteria.

Bigham, in U.S. Pat. No. 4,244,951 issued Jan. 13, 1981; and Netherland Patent Application No. 8,000,775 published Aug. 15, 1980, corresponding to British Patent Application No. 2,044,255 both disclose novel conjugates of penicillanic acid 1,1-dioxide with known penicillin antibiotics which are linked via a methylenedioxy group. These conjugates are of the general formula

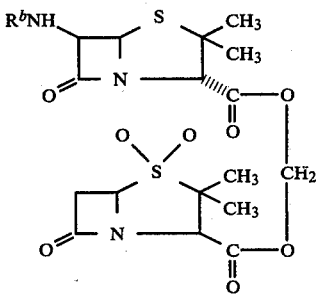

wherein $R^b$ is the acyl group of a natural or semisynthetic penicillin.

The compound of the above formula wherein $R^b$ is D-(2-amino-2-phenylacetyl) is designated herein as "sultamicillin" and will be referred to herein by that name. It is a methylenedioxy linked conjugate of penicillanic acid 1,1-dioxide and ampicillin.

Sultamicillin free base has been found to have poor handling characteristics and inadequate stability. The only salt of sultamicillin specifically disclosed in the art is the hydrochloride. While it is suitable for certain antibacterial formulations, it also has poor solid state stability, which is reflected in handling difficulties, and is highly soluble in water in which it is subject to hydrolytic decomposition. Thus, it is unsuitable for aqueous dosage formulations, including the aqueous suspensions preferred in pediatric medicine.

Crystalline forms of compounds are ordinarily preferable to the non-crystalline forms thereof. The crystalline materials have superior stability, appearance and handling characteristics when compared to their amorphous counterparts. For pharmaceutical use crystalline compounds are especially advantageous in manufacturing procedures and in formation and use of acceptable dosage forms such as solutions, suspensions, elixirs, tablets, capsules and various pharmaceutically elegant preparations required by the medical and pharmaceutical professions.

For pediatric administration it is well recognized by those of skill in the art that solutions or liquid suspensions are highly preferable dosage forms. Tablets and capsules are difficult for children to swallow and the amount of drug delivered is not as flexible as is often required for pediatric drugs. With liquid dosage forms, by contrast, the amount of drug delivered to the patient can be varied over a wide range merely by regulating the volume of dose of known concentrations.

Conjugate antibiotics such as sultamicillin are susceptible to partial hydrolysis to its components (ampicillin and sulbactam) upon storage in aqueous media. Thus, the enhanced stability in aqueous suspensions of a salt of sultamicillin of limited solubility, relative to another salt of significantly higher solubility, such as the hydrochloride, is evident.

SUMMARY OF THE INVENTION

The invention relates to certain benzenesulfonic acid addition salts of sultamicillin of the formula

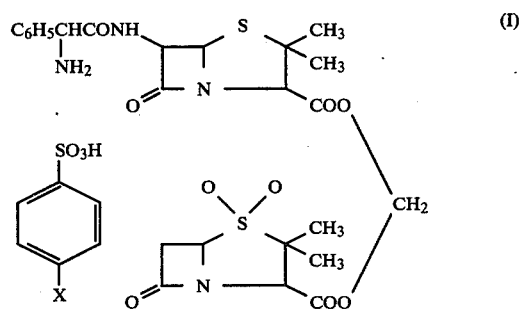

and hydrated forms thereof, where X is hydrogen or chloro. Especially preferred salts of formula (I) are the crystalline dihydrates. These crystalline salts have advantages over prior art forms of sultamicillin and other salts of this conjugate antibacterial agent. The crystalline dihydrate salts of the invention have excellent pharmacokinetic properties, near optimal solubility in aqueous systems and improved stability in bulk and in aqueous suspensions. As a result of these features, the crystalline salts of the invention offer valuable advantages in manufacture of various dosage forms, particularly pediatric dosage forms, and in improving product stability.

The invention also provides the anhydrous and other hydrated forms of the same salts of formula (I) which serve as precursors of the more desirable crystalline dihydrates.

The invention also provides pharmaceutical compositions suitable for treating a bacterial infection in a mammalian subject comprising an antibacterially effective amount of a crystalline dihydrate salt of the invention and a pharmaceutically acceptable carrier. Particularly preferred such compositions are those suitable for use in pediatric medicine.

Further, the invention provides a method for treating a bacterial infection in a mammalian subject, especially a child, which comprises administering to said subject an antibacterially effective amount of a salt of the invention.

DETAILED DESCRIPTION OF THE INVENTION

The salts of formula (I) are prepared by standard methods known in the art for preparing acid addition salts of aminopenicillins. For example, they are obtained by contacting the free base of sultamicillin with an equimolar amount of the appropriate acid, i.e., benzenesulfonic acid or 4-chlorobenzenesulfonic acid in the presence of a suitable solvent. By the term "suitable solvent" is meant a solvent that will not appreciably react with the reactants or product, under the conditions employed, except to form a solvate, will dissolve or partially dissolve the reactants at or about room temperature and will allow precipitation of the product salt at room temperature or below, or upon addition of a nonsolvent. Examples of suitable solvents include ethyl acetate, methanol, ethanol, butanol, acetone, methylethyl ketone, tetrahydrofuran, water and mixtures thereof. The sultamicillin free base can be obtained, e.g., by methods described in U.S. Pat. No. 4,244,951 and Great Britain Patent Application No. 2,044,255. The starting benzenesulfonic acids are readily available in commerce.

The compounds of formula (I) can also be prepared by metathesis of salt forms in which an inorganic salt is formed, for example, by reaction of a hydrohalide addition salt of sultamicillin with an alkali metal or alkaline earth salt of the appropriate sulfonic acid. In a preferred such reaction, sultamicillin hydrochloride is reacted with sodium benzenesulfonate or sodium 4-chlorobenzenesulfonate in water, from which the particularly preferred crystalline dihydrate salt of formula (I) is precipitated and, if desired further purified, e.g. by recrystallization.

A further method for forming the instant salts of formula (I) is by reaction of an amino-protected precursor of sultamicillin in the presence of the requisite benzenesulfonic acid or 4-chlorobenzenesulfonic acid under conditions which both remove the aminoprotecting group and allow salt formation. In a preferred such reaction an enamine-protected precursor of sultamicillin, e.g. 1,1-dioxopenicillanoyloxymethyl 6-[D-(2-[1-methyl-2-methoxycarbonylvinylamino]-2-phenylacetamido)]penicillanate is contacted with an equimolar amount of benzenesulfonic acid or 4-chlorobenzenesulfonic acid in the presence of a polar organic solvent, e.g., ethyl acetate, and water. Under these conditions and at or about room temperature, the enamine protecting group is removed, the desired salt is formed and it precipitates from solution, ordinarily as the crystalline dihydrate.

When salt formation is carried out under anhydrous conditions, the product formed is an anhydrous compound of formula (I). When the amount of water used is less than that needed to form the dihydrate mixtures of the anhydrous, monohydrate and dihydrate forms are produced. The anhydrous salts and monohydrates of formula (I) are useful as intermediates leading to the more stable dihydrates upon exposure to moisture.

The crystalline dihydrate salts of the invention have advantageous properties which make them particularly useful as orally administered antibacterial agents. They allow rapid absorption from the gastrointestinal tract. During or subsequent to absorption, in vivo ester hydrolysis occurs with liberation of ampicillin and the beta-lactamase inhibitor, penicillanic acid 1,1-dioxide (sulbactam). These salts have relatively low, yet adequate, solubility in aqueous systems, resulting in improved stability of aqueous oral dosage forms, such as the oral suspensions preferred in pediatric medicine.

Pharmacokinetic Studies

Upon oral administration to laboratory animals the crystalline invention compounds and the hydrochloride salt are each found to have excellent pharmacokinetic properties. The results of such a study conducted in rats is summarized in Table I, below. The data shows that each of the three salts are rapidly absorbed and hydrolyzed upon oral administration to produce high serum levels of both ampicillin and the beta-lactamase inhibitor, sulbactam. The differences between the three salts summarized in Table I are found to be not significant, statistically.

TABLE I

Pharmacokinetic Data After Oral Administration of 20 mg./kg. of Sultamicillin Salt to Rats

| Sample Time, Hr. | Serum Concentration (μg./ml.) | | | | | |
|---|---|---|---|---|---|---|
| | Hydrochloride Salt | | $C_6H_5SO_3H \cdot 2H_2O$ Salt | | $4\text{-}ClC_6H_4SO_3H \cdot 2H_2O$ Salt | |
| | Ampicillin | Sulbactam | Ampicillin | Sulbactam | Ampicillin | Sulbactam |
| 0.25 | 1.74 ± 0.15 | 1.51 ± 0.27 | 1.77 ± 0.17 | 1.15 ± 0.13 | 2.65 ± 0.26 | 2.21 ± 0.32 |
| 0.5 | 1.99 ± 0.17 | 2.15 ± 0.30 | 2.25 ± 0.16 | 1.47 ± 0.20 | 2.88 ± 0.03 | 2.29 ± 0.24 |
| 1 | 1.39 ± 0.12 | 1.46 ± 0.12 | 1.31 ± 0.07 | 1.00 ± 0.11 | 1.47 ± 0.18 | 1.13 ± 0.12 |
| 1.5 | 0.87 ± 0.11 | 1.00 ± 0.16 | 0.80 ± 0.01 | 0.67 ± 0.11 | 0.81 ± 0.07 | 0.73 ± 0.05 |
| 2 | 0.5 ± 0.07 | 0.71 ± 0.13 | 0.55 ± 0.03 | 0.49 ± 0.07 | 0.39 ± 0.06 | 0.39 ± 0.03 |
| 3 | 0.25 ± 0.04 | 0.42 ± 0.08 | 0.26 ± 0.02 | 0.34 ± 0.05 | 0.15 ± 0.03 | 0.16 ± 0.03 |
| 4 | 0.13 ± 0.02 | 0.17 ± 0.04 | 0.15 ± 0.01 | 0.22 ± 0.02 | 0.06 ± 0.0007 | 0.08 ± 0.01 |
| Area Under Serum Curve, μg./ml. hr. | 3.19 | 3.96 | 3.28 | 2.91 | 3.42 | 2.92 |
| T ½, Beta-phase, hr. | 0.87 | 1.18 | 0.91 | 1.26 | 0.63 | 0.73 |

The above data was obtained employing 80–100 g. out-bred Sprague-Dawley rats. The compounds are administered orally (5 rats per compound) as an aqueous suspension, 0.5 ml., containing 20 mg./kg. of the drug.

Blood samples are taken at the indicated times and subjected to differential bioassay to determine the ampicillin and sulbactam levels. The ampicillin bioassay makes use of *Sarcina lutea* (ATCCC 9341) which is susceptible to ampicillin but insensitive to sulbactam at concentrations as high as 100 μg./ml., since it does not contain a beta-lactamase. Thus, this organism fails to show synergy with combinations of ampicillin and sulbactam. A standard curve is prepared in normal serum at ampicillin levels of 4, 2, 1, 0.5, 0.25 and 0.125 μg.ml. Sterile filter paper discs are loaded with 25 lambda volumes. Assay plates are prepared using seed agar (Difco). An overnight culture of *Sarcina lutea* is diluted 1:100 and 1 ml. of this dilution is added to 100 ml. of the agar in 12/12" plastic plates. The plates are then incubated at 37° C. for 18 hours, and the zones measured.

The sulbactam determination is based on the insensitivity of *Pasteurella histolytica* (59B010) to high concentrations of either ampicillin or sulbactam, alone. However, since its resistance is mediated via a beta-lactamase, the culture responds synergistically to combinations of ampicillin and sulbactam. A standard curve is prepared in a manner analogous to that described above for ampicillin. Assay plates are prepared by adding 1 ml. of an overnight culture of *Pasteurella histolytica* to 100 ml. of Mueller-Hinton agar that has been adjuncted with 50 μg./ml. ampicillin and 5% sterile bovine blood. The plates are incubated at 37° C. for about 18 hours after which the zones are measured.

Solubility

The solubility of the salts in water and simulated gastric juice without pepsin (pH 1.2) were compared. Equilibrium solubility was not determined since the compounds are not entirely stable in aqueous systems for the extended time required to reach equilibrium. Therefore, the apparent solubility was determined by vigorous agitation for 30 minutes with the solvent. The resulting mixture was then filtered and the amount of compound in solution determined by high pressure liquid chromatography (HPLC). The results are summarized in Table II.

TABLE II

Apparent Solubility of Sultamicillin Salts in Water and Simulated Gastric Juice (Without Pepsin, pH 1.2)

| Salt | Apparent Solubility, mg/ml | | | |
|---|---|---|---|---|
| | Water | (Final pH) | Simulated Gastric Juice | (Final pH) |
| Hydrochloride | >94 | (2.0) | >79 | (1.12) |
| Benzenesulfonate.2H$_2$O* | 2.15 | (.34) | 1.8 | (2.0) |
| 4-Chlorobenzene-sulfonate.2H$_2$O* | 3.3 | (3.8) | 6.3 | (1.1) |

*crystalline

Crystallinity

X-ray powder diffraction patterns were obtained on a Siemens diffractometer equipped with copper radiation and a scintillation counter detector. Beam intensity as a function of the angle 2 theta was recorded at a scanning rate of 2° per minute. The crystallinity of sultamicillin benzenesulfonate dihydrate and sultamicillin 4-chlorobenzenesulfonate dihydrate were verified by a multiplicity of peaks in the x-ray powder diffraction patterns for these salts.

Stability

Upon storage of samples of the three salts at 50° C. for three weeks the crystalline benzenesulfonate.2H$_2$O and 4-chlorobenzenesulfonae.2H$_2$O were found to have retained 97% and 100% of their potency, respectively. The hydrochloride salt retained only 67% of its original potency under these conditions.

High Pressure Liquid Chromatography (HPLC)

In the solubility and stability studies above samples of the materials were assayed by HPLC using a Chromegabond C-8* column (4.6 mm internal diameter×30 cm.). The mobile phase consisted of 30% by weight acetonitrile in pH 3 phosphate buffer (0.1 M). Flow rate, 1.6 ml/minute. Detection was by UV at 230 nm.
*A trademark of ES Industries.

When using an antibacterial salt of this invention in a mammal, particularly man, the compound can be administered alone, or it can be mixed with other antibiotic substances and/or pharmaceutically-acceptable carriers or diluents. Said carrier or diluent is chosen on the basis of the intended mode of administration. For example, when considering the oral mode of administration, an antibacterial compound of this invention can be used in the form of tablets, capsules, lozenges, troches, powders, syrups, elixirs, aqueous solutions and suspensions, and the like, in accordance with standard pharmaceutical practice. The proportional ratio of active ingredient to carrier will naturally depend on the chemical nature, solubility and stability of the active ingredient, as well as the dosage contemplated. In the case of tablets for oral use, carriers which are commonly used include lactose, sodium citrate and salts of phosphoric acid. Various disintegrants such as starch, and lubricating agents, such as magnesium stearate, sodium lauryl sulfate and talc, are commonly used in tablets. For oral administration in capsule form, useful diluents are lactose and high molecular weight polyethylene glycols, e.g. polyethylene glycols having molecular weights of from 2000 to 4000.

Because of the advantageous solubility and stability of the crystalline sultamicillin benzenesulfonate dihydrate salts of the invention, a particularly preferred mode of administration for use with children is orally via an aqueous suspension. For preparing such suspensions the crystalline dihydrate of formula (I) can be combined with buffers, emulsifying and suspending agents. If desired, certain sweetening and/or flavoring agents can be added. The resulting suspension can be stored in the presence of water, especially if refrigerated, for considerable periods. However, a preferred method is to store the mixture as a dry powder until its use is required, at which time it is mixed with an appropriate diluent, e.g., water.

As indicated earlier, the antibacterial compounds of this invention are of use in human subjects and the daily dosages to be used will not differ significantly from other, clinically-used, penicillin antibiotics. The prescribing physician will ultimately determine the appropriate dose for a given human subject, and this can be expected to vary according to the age, weight, and response of the individual patient as well as the nature and severity of the patient's symptoms. The compounds of this invention will normally be used orally at dosages in the range from about 20 to about 100 mg. per kilogram of body weight per day, and parenterally at dosages from about 10 to about 100 mg. per kilogram of body weight per day, usually in divided doses. In some instances it may be necessary to use doses outside these ranges.

The following examples and preparations are provided solely for further illustration. Infrared (IR) spectra were measured as potassium bromide discs (KBr discs) and diagnostic absorption bands are reported in wave numbers (cm$^{-1}$). Nuclear magnetic resonance spectra (NMR) were measured at 60 MHz for solutions in deuterated chloroform (CDCl$_3$) or deuterated dimethyl sulfoxide (DMSO-d$_6$), and peak positions are reported in parts per million downfield from tetramethylsilane. The following abbreviations for peak shapes are used: s, singlet; d, doublet; t, triplet; q, quartet; m, multiplet.

EXAMPLE 1

1,1-Dioxopenicillanoyloxymethyl 6-[D-(2-amino-2-phenylacetamido)]penicillanate benzenesulfonate dihydrate To 6.31 g. (0.01 mole) 1,1-dioxopenicillanoyloxymethyl 6-[D-(2-amino-2-phenylacetamido)]penicillanate hydrochloride is added 40 ml. water and the mixture is stirred for about 15 minutes. Insoluble material (ca. 0.75 g. of gum) is removed by filtration and to the filtrate is added a solution of 1.58 g. (0.01 mole) benzenesulfonic acid in 10 ml. water. The resulting gummy mixture is stirred with a glass rod until the salt hardens and breaks up into small lumps. Stirring is continued for one hour (magnetic stirrer) after which the solid is collected by filtration and washed well with water. The washed solid is dried under nitrogen to afford 5.8 g. (77%) of colorless product, M.P. 138° C. (decomp.). $^1$H-NMR (DMSO-$d_6$) ppm (delta): 1.38 (s, 6H), 1.45 (s, 6H), 3.0–3.9 (m, 2H), 4.4 (s, 1H), 4.5 (s, 1H), 4.95–5.28 (m, 2H), 5.3–5.66 (m, 2H), 5.89 (s, 2H), 7.15–7.75 (m, 10H); infrared spectrum: (Nujol*) broad band at 1805–1770 cm$^{-1}$.

*Trademark for Plough Inc. brand of Mineral Oil.

X-ray powder diffraction: peaks, degrees 2 theta: 9.3, 11.4, 12.2, 13.4, 15.5, 16.2, 16.9, 17.1, 18.3, 18.9, 19.8, 20.6, 22.3, 22.7, 23.4, 25.4, 26.7, 27.3, 29.6, 30.5, 31.7, 33.5, 34.4, 35.1, 36.1, 37.5, 38.6 and 44.7.

EXAMPLE 2

1,1-Dioxopenicillanoyloxymethyl 6-[D-(2-amino-2-phenylacetamido)]penicillanate 4-chlorobenzenesulfonate dihydrate To a solution of 15 g. (25.25 mmole) 1,1-dioxopenicillanoyloxymethyl 6-[D-(2-amino-2-phenylacetamido)]-penicillanate in 150 ml. ethyl acetate is added over ten minutes a solution of 4.85 g. (25.25 mmole) 4-chlorobenzenesulfonic acid in 25 ml. ethyl acetate and 6 ml. water. After the addition is complete, an additional 50 ml. ethyl acetate is added and the resulting mixture is stirred at room temperature overnight. The colorless crystals are collected by filtration, the cake slurried in 200 ml. ethyl ether and filtered again. Upon drying in air 13.7 g. of colorless crystals are obtained.

Ten grams of crystals are dissolved in 100 ml. methanol at room temperature. Water is added to the cloud point (ca. 200 ml.). The resulting hazy solution is stirred at room temperature for two hours during which time the product crystallizes. Upon filtration and air drying overnight, 7.5 g. of product is obtained. $^1$H-NMR (DMSO-$d_6$) ppm (delta): 1.36 (s, 6H), 1.47 (s, 6H), 3.34 (broad, 5H), 3.74 (dd, 1H, J=4 Hz, 17 Hz), 4.40 (s, 1H), 4.51 (s, 1H), 5.08 (m, 2H), 5.48 [m, 2H, ($J_{ABq}$=4 Hz upon D$_2$O overlay)], 5.86 (s, 2H), 7.45 (m, 9H).

Analysis Calculated for $C_{31}H_{35}O_{12}N_4S_3Cl.2H_2O$: C, 45.22; H, 4.77; N, 6.81; S, 11.68; Cl, 4.31. Found: C, 45.04; H, 4.83; N, 6.86; S, 11.74; Cl, 4.27.

Water (Karl Fischer) 4.98 (Theory, 4.37).

X-ray powder diffraction: peaks, degrees 2 theta: 8.9, 10.8, 11.3, 13.2, 15.5, 16.0, 17.1, 18.0, 19.3, 20.0, 22.4, 22.7, 23.3, 26.0, 27.9, 30.0, 30.5, 34.1, 34.5, 35.9, 37.5, 38.5 and 44.8.

EXAMPLE 3

To a stirred mixture of 6.31 g (0.01 mole) 1,1-dioxopenicillanoyloxymethyl 6-[D-(2-amino-2-phenylacetamido)]penicillanate hydrochloride in 100 ml. acetone is added a solution of 1.01 g. (0.01 mole) triethylamine in 25 ml. tetrahydrofuran and stirring is continued for 15 minutes. The insoluble material is removed by filtration and washed with acetone. The combined filtrate and washings are concentrated in vacuo to ca. 100 ml. and a solution of 1.58 g. (0.01 mole) benzenesulfonic acid in 10 ml. ethanol is added slowly at room temperature. The resulting mixture is stirred while concentrating in vacuo to about half volume. The concentrated mixture is stirred while cooling in an ice-water bath until precipitation is complete. Filtration, washing with cold acetone, then ethyl ether and air drying affords crystals of the desired benzenesulfonate salt of 1,1-dioxopenicillanoyloxymethyl 6-[D-(2-amino-2-phenylacetamido)]penicillanate.

Use of 4-chlorobenzenesulfonic acid in place of benzenesulfonic acid in the above procedure affords the corresponding crystalline 4-chlorobenzenesulfonate salt.

EXAMPLE 4

A mixture of 6.31 g. (0.01 mole) 1,1-dioxopenicillanoyloxymethyl 6-[D-(2-amino-2-phenylacetamido)]-penicillanate hydrochloride and 40 ml. water are stirred for 20 minutes and filtered. To the filtrate is added slowly a solution of 1.80 g. (0.01 mole) sodium benzenesulfonate in 10 ml. water. The resulting mixture is stirred for two hours, filtered, the cake washed with water and dried in the vacuum oven at 45° C. to provide the desired crystalline benzenesulfonate dihydrate of 1,1-dioxopenicillanoyloxymethyl 6-[D-(2-amino-2-phenylacetamido)]penicillanate.

Use of potassium 4-chlorobenzenesulfonate in place of sodium benzenesulfonate in the above procedure provides 1,1-dioxopenicillanoyloxymethyl 6-[D-(2-amino-2-phenylacetamido)]penicillanate 4-chlorobenzenesulfonate, which upon recrystallization from methanol/water by the method of Example 2 affords the crystalline dihydrate.

EXAMPLE 5

To a solution of B 693 mg. (1 mmole) 1,1-dioxopenicillanoyloxymethyl 6-[D-(2-[1methyl-2-methoxycarbonylvinylamino]-2-phenylacetamido)]penicillanate in 30 ml. ethyl acetate is added a solution of 158 mg. (1 mmole) benzenesulfonic acid in 5 ml. water and the mixture is stirred for 45 minutes. The precipitated product is collected by filtration, washed with water and dried in the vacuum oven at 40° C. to provide the crystalline benzenesulfonate dihydrate salt of sultamicillin.

Use of 4-chlorobenzenesulfonic acid in place of benzenesulfonic acid provides crystals of the 4-chlorobenzenesulfonate dihydrate salt of sultamicillin.

EXAMPLE 6

A solution of 64.1 g. (0.108 mole) 1,1-dioxopenicillanoyloxymethyl 6-[D-(2-amino-2-phenylacetamido)]-penicillanate in 1400 ml. ethyl acetate (apparent pH 7.6) is adjusted to pH 2.5 by addition of 325 ml. of a solution of 18.0 g. benzenesulfonic acid (90% technical grade) in 400 ml. ethyl acetate. The resulting pale yellow slurry is cooled to 5° C. and granulated for 60 minutes at this temperature. The resulting slurry is washed with an equal volume of water, the layers separated and the ethyl acetate layer is cooled to 5° C. The resulting thick white slurry is filtered, the cake washed with hexane (4×100 ml.) and dried in vacuo at 35° C. overnight to afford 42 g. of crystalline benzenesulfonate salt which assayed 4.67% water (Karl Fischer method); % volatiles (60° C., 3 hours in vacuo), 5.00%.

Analysis, Calculated for $C_{31}H_{36}O_{12}N_4S_3.2H_2O$): C, 47.20; H, 5.11; N, 7.10; S, 12.19. Found: C, 47.14; H, 5.21; N, 7.12; S, 11.92.

EXAMPLE 7

Anhydrous 1,1-Dioxopenicillanoyloxymethyl 6-[D-(2-amino-2-phenylacetamido)]penicillanate benzenesulfonate To a solution of 594 mg. (1 mmole) 1,1-dioxopenicillanoyloxymethyl 6-[D-(2-amino-2-phenylacetamido)]-penicillanate in 40 ml. of dry ethyl acetate is added a solution of 158 mg. anhydrous benzenesulfonic acid in 10 ml. dry ethyl acetate. After stirring at room temperature under anhydrous conditions for 30 minutes, the solvent is evaporated to a small volume and the precipitated anhydrous salt is collected by filtration and dried in vacuo over phosphorous pentoxide for 6 hours.

Upon storage of the anhydrous salt at 50% relative humidity for 30 hours the product forms the dihydrate containing 4.5% water, by weight.

When 4-chlorobenzenesulfonic acid is used in the above procedure the corresponding anhydrous 4-chlorobenzenesulfonic acid addition salt is obtained. It also forms a dihydrate upon exposure to atmospheric moisture for 48 hours.

EXAMPLE 8

Tablets

A tablet base is prepared by blending the following ingredients:

|  | Parts by Weight |
| --- | --- |
| Sucrose, U.S.P. | 80.3 |
| Tapioca starch | 13.2 |
| Magnesium stearate | 6.5 |

Into this base is blended a sufficient amount of crystalline 1,1-dioxopenicillanoyloxymethyl 6-[D-(2-amino-2-phenylacetamido)]penicillanate benzenesulfonate dihydrate to provide tablets containing 100, 250 and 500 mg. of active ingredient.

EXAMPLE 9

A blend of the following ingredients is prepared:

|  | Weight, grams |
| --- | --- |
| Citric acid | 20.0 |
| Sodium citrate | 5.0 |
| Magnesium trisilicate, U.S.P. | 5.0 |
| Lactose, U.S.P. | 7.5 |
| Potato starch | 7.5 |
| Magnesium stearate | 0.8 |

To this blend is added an additional 0.4 g. magnesium stearate and sufficient crystalline sultamicillin 4-chlorobenzenesulfonate dihydrate to provide capsules containing 100, 500 and 1000 mg. of active ingredient.

EXAMPLE 10

Oral Suspension

A dry blend of the following ingreidents is prepared:

|  | Grams |
| --- | --- |
| Sultamicillin benzenesulfonate dihydrate, crystalline | 6.80 |
| Sucrose | 20.00 |
| Mannitol | 10.00 |
| Sodium citrate | 0.40 |
| Hydrated aluminum magnesium silicate powder (Veegum S) | 5.00 |
| Kaolin | 2.00 |
| Sodium saccharin | 2.00 |
| Artificial flavor, powder | 0.10 |

The dry blend is stored in sealed containers until needed, at which time it is diluted to 100 ml. volume with water. The suspension contains the equivalent of 50 mg./ml. of sultamicillin.

PREPARATION A

Chloromethyl Penicillanate 1,1-Dioxide

A mixture of 4.66 g. of penicillanic acid 1,1-dioxide, 50 ml. of dichloromethane and 35 ml. of water was treated with sufficient tetrabutylammonium hydroxide (40% in water) to give a pH of 6.0. The dichloromethane layer was separated and the aqueous phase extracted with fresh dichloromethane (2×50 ml.). The organic layers were combined, dried over sodium sulfate and concentrated to give 10.1 g. of the tetrabutylammonium salt of penicillanic acid 1,1-dioxide.

The above tetrabutylammonium penicillanate 1,1-dioxide was added to 50 ml. of chloroiodomethane and the reaction mixture allowed to stir at ambient temperature overnight. The reaction mixture was concentrated to half volume in vacuo, and chromatographed on 200 g. of silica gel using ethyl acetate/hexane as the eluant, 12 ml. cuts being taken every 30 seconds. Fractions 41-73 were combined and concentrated to dryness to give 3.2 g. of the title compound.

The NMR spectrum ($CDCl_3$) showed absorptions at 1.5 (s, 3H), 1.66 (s, 3H), 3.42 (d, 2H), 4.38 (s, 1H), 4.6 (t, 1H) and 5.7 (dd, 2H) ppm.

PREPARATION B

Iodomethyl Penicillanate 1,1-Dioxide

To a solution of 7.9 g. of chloromethyl penicillanate 1,1-dioxide in 100 ml. of dry acetone maintained under a nitrogen atmosphere was added 21.0 g. of sodium iodide, and the reaction mixture was allowed to stir overnight at room temperature. The reaction mixture was concentrated in vacuo, and the residue was dissolved in 150 ml. ethyl acetate and 150 ml. water. The organic layer was separated and the aqueous layer was extracted with fresh ethyl acetate. The organic extracts were combined, washed with water (1×500 ml.) and brine (1×50 ml.) and dried over sodium sulfate. Removal of the solvent gave 10.5 g. of the title product, m.p. 100°–102° C.

The NMR spectrum ($CDCl_3$) showed absorptions at 1.55 (s, 3H), 1.68 (s, 3H), 3.5 (d, 2H), 4.4 (s, 1H), 4.65 (t, 1H) and 6.0 (dd, 2H) ppm.

PREPARATION C

Tetrabutylammonium 6-[D-(2-[1-methyl-2-methoxycarbonylvinylamino]-2-phenylacetamido)]penicillanate To 300 ml. chloroform is added 39.3 g. 6-[D-(2-amino-2-phenylacetamido)]penicillanate acid trihydrate, 50 ml. of water is added and the pH of the mixture adjusted to 8.5 by addition of 40% aqueous tetrabutylammonium hydroxide. The layers are separated, the aqueous layer is saturated with sodium sulfate and extracted with fresh chloroform. The extracts and initial lower layer are combined and the solvent is evaporated to about 250 ml. total volume.

To this is added 150 ml. methyl acetoacetate and 30 g. of anhydrous magnesium sulfate. The mixture is heated at reflux for three hours, the mixture allowed to settle and the warm organic layer decanted. The chloroform is evaporated, ethyl acetate (500 ml.) added and the solution is allowed to cool to precipitate the title compound in 52% yield, m.p. 182°–184° C. (decomp.). $^1$H-NMR (CDCl$_3$) ppm (delta): 0.8–2.0 (m, 4H), 1.88 (s, 3H), 3.1–3.6 (m, 8H), 3.6 (s, 3H), 4.17 (s, 1H), 4.58 (s, 1H), 5.05 (d, 1H), 5.38–5.6 (m, 2H), 6.78 (d, 1H), 7.35 (s, 5H), 9.4 (d, 1H).

PREPARATION D 1,1-Dioxopenicillanoyloxymethyl 6-[D-(2-[1-methyl-2-methoxycarbonylvinylamino]-2-phenylacetamido)]penicillanate To 35 ml. dimethylformamide is added 1.86 g. (0.005 mole) iodomethyl 1,1-dioxopenicillanate and 3.44 g. (0.005 mole) tetrabutylammonium 6-[D-(2-[1-methyl-2-methoxycarbonylvinylamino]-2-phenylacetamido)]penicillanate and the mixture is stirred at room temperature for two hours. Ethyl acetate (150 ml.) is added, the mixture washed with brine, water, brine again, dried (Na$_2$SO$_4$) and concentrated in vacuo.

PREPARATION E 1,1-Dioxopenicillanoyloxymethyl 6-[D-(2-amino-2-phenylacetamido)]penicillanate hydrochloride and free base To a solution of 3.465 g. (0.005 mole) 1,1-dioxopenicillanoyloxymethyl 6-[D-(2-[1-methyl-2-methoxycarbonylvinylamino]-2-phenylacetamido)]penicillanate in 50 ml. acetone is added 5.5 ml. of 1.0 N hydrochloric acid, 5 ml. water and the mixture is stirred at room temperature for 30 minutes. The acetone is evaporated in vacuo, the aqueous residue washed with ethyl ether, filtered and lyophilized to give the hydrochloride salt of the title compound.

Alternatively, the aqueous residue from evaporation of the acetone is washed with ethyl acetate and ethyl ether. Methylene chloride is added to the aqueous layer, the mixture is cooled and 460 mg. sodium bicarbonate is added in portions. The aqueous phase is separated, extracted again with methylene chloride, the combined organic layers are dried (MgSO$_4$) and the solvent evaporated in vacuo to provide the title free base.

We claim:
1. A benzenesulfonic acid addition salt of sultamicillin of the formula

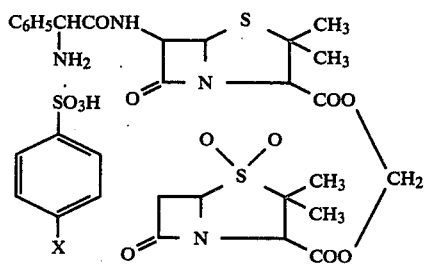

and hydrated forms thereof, wherein X is hydrogen or chloro.

2. A crystalline dihydrate salt according to claim 1.
3. The crystalline dihydrate salt according to claim 2 wherein X is hydrogen, having the following X-ray powder diffraction peaks:

| Peak, degrees 2 theta | | |
|---|---|---|
| 9.3 | 19.8 | 30.5 |
| 11.4 | 20.6 | 31.7 |
| 12.2 | 22.3 | 33.5 |
| 13.4 | 22.7 | 34.4 |
| 15.5 | 23.4 | 35.1 |
| 16.2 | 25.4 | 36.1 |
| 16.9 | 26.7 | 37.5 |
| 17.1 | 27.3 | 38.6 |
| 18.3 | 29.6 | 44.7 |
| 18.9 | | |

4. The crystalline salt according to claim 2 wherein X is chloro, having the following X-ray powder diffraction peaks:

| Peak, degrees 2 theta | | |
|---|---|---|
| 8.9 | 19.3 | 30.5 |
| 10.8 | 20.0 | 34.1 |
| 11.3 | 22.4 | 34.5 |
| 13.2 | 22.7 | 35.9 |
| 15.5 | 23.3 | 37.5 |
| 16.0 | 26.0 | 38.5 |
| 17.1 | 27.9 | 44.8 |
| 18.0 | 30.0 | |

5. A pharmaceutical composition suitable for treating a bacterial infection in a mammalian subject, which comprises an antibacterially effective amount of a compound according to claim 2 and a pharmaceutically acceptable carrier.

6. A pharmaceutical composition according to claim 5 in the form of an aqueous suspension for oral administration to children.

7. A method of treating a bacterial infection in a mammalian subject, which comprises administering thereto an antibacterially effective amount of a compound according to claim 1.

8. A method according to claim 7 wherein said subject is a child.

* * * * *